United States Patent

Reiss et al.

Patent Number: 5,064,614
Date of Patent: Nov. 12, 1991

[54] METHOD FOR STERILIZING HEAT-TOLERATING CONTAINERS UNDER CLEAN-ROOM CONDITIONS

[75] Inventors: Roland Reiss; Gerd Liskow; Hinrich Gehrke; Walter Luxner; Gerd Schmidt; Dieter Winiarski, all of Berlin; Eckehart Lindner, Odenthal-Hahnenberg; Edgar Sirch, Leverkusen; Eckhard Kalbfleisch, Leverkusen; Hans Laubert, Leverkusen; Peter Kiefer, Odenthal-Glöbusch; Johann Franz, Leverkusen; Anton Fasse, Pulheim, all of Fed. Rep. of Germany

[73] Assignee: Hans Gilovyy Maschinenfabrik "Meteorwerk" GmbH & Co., Berlin, Fed. Rep. of Germany

[21] Appl. No.: 256,989

[22] Filed: Oct. 13, 1988

[30] Foreign Application Priority Data

Oct. 14, 1987 [DE] Fed. Rep. of Germany ....... 3734830

[51] Int. Cl.[5] .............................................. A61L 2/06
[52] U.S. Cl. .................................... 422/22; 422/32; 422/33; 422/108; 422/111; 422/112; 422/300; 422/304
[58] Field of Search ............... 98/40.1, 40.11, 33.1; 422/22, 24, 32, 33, 109, 110, 112, 300, 304, 306, 111

[56] References Cited

U.S. PATENT DOCUMENTS

| | | | |
|---|---|---|---|
| 3,824,909 | 7/1974 | Horneff et al. | 98/40.1 |
| 3,961,150 | 6/1976 | Lewis et al. | 422/22 |
| 4,140,479 | 2/1979 | Sirch et al. | 422/304 |
| 4,175,934 | 11/1979 | Lang et al. | 98/33.1 |

FOREIGN PATENT DOCUMENTS 3321195 12/1984 Fed. Rep. of Germany .

Primary Examiner—Robert J. Warden
Assistant Examiner—Timothy M. McMahon
Attorney, Agent, or Firm—Nies, Kurz, Bergert & Tamburro

[57] ABSTRACT

The containers which are to be sterilized (glass bottles) (1) are continuously moved into and out of a radiant oven via laminar-flow units and then cooled in a cooling zone by HOSCH-filtered air. A part of the HOSCH-filtered cooling air is here branched off and passed through the radiant oven in a low-turbulence counterflow. At the entry of the bottles into the radiant oven, this counterflow is extracted by means of a fumes/exit air fan (11). The required clean-room conditions are maintained in the radiant oven by a positive pressure $P_2$ as compared with atmospheric pressure $P_{AT}$ and a thus resulting counterflow of a means flow velocity of <0.2 m/second is maintained. The positive pressure $P_2$ is here measured in the radiant oven and compared with the set value, and the exit fan (11) air for the HOSCH-filtered cooling air on the exit side is reregulated in such a way that the deviation $\Delta p$ from the set value is minimized. In addition, provision is made for the major part of the radiant heater elements (4) being operated at constant electric power and for eliminating the temperature fluctuations caused by unsteady operating states by controlling the remaining part of the heater elements (4).

8 Claims, 1 Drawing Sheet

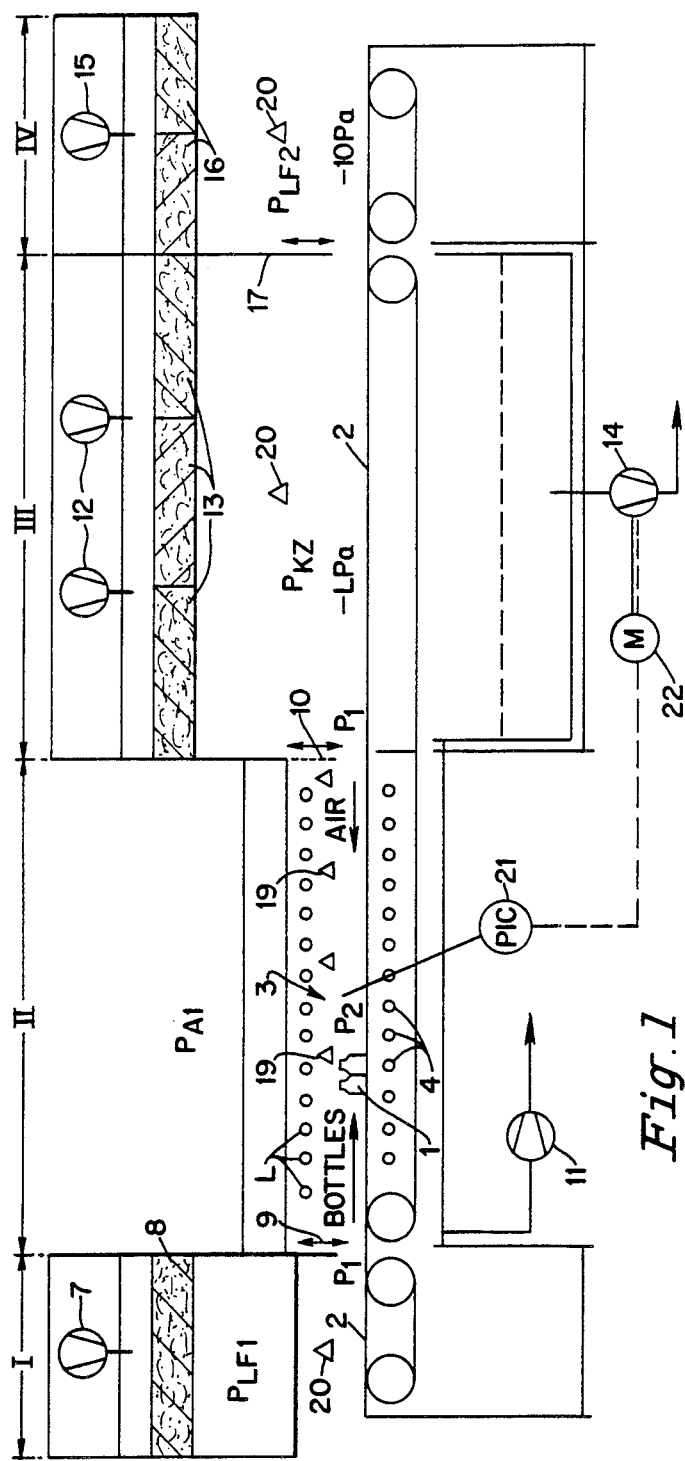
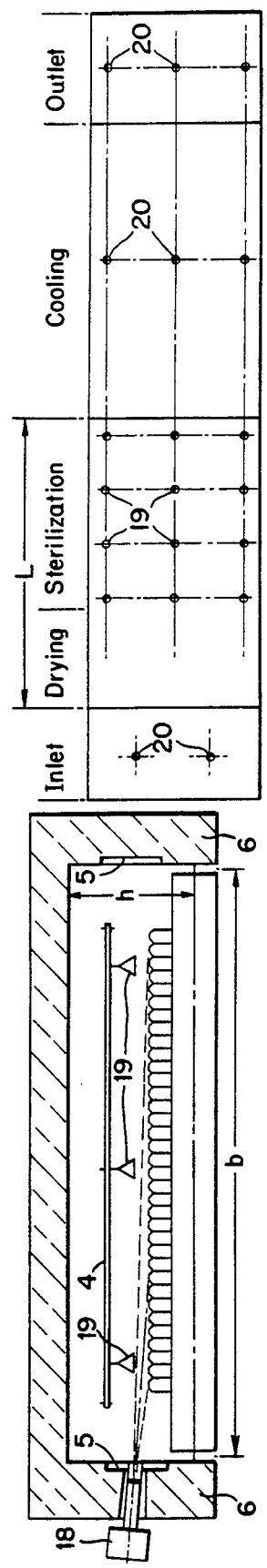
Fig.1
Fig.2
Fig.3

METHOD FOR STERILIZING HEAT-TOLERATING CONTAINERS UNDER CLEAN-ROOM CONDITIONS

BACKGROUND OF THE INVENTION

The invention starts from a method for dry-heat sterilization of heat-tolerating containers under clean-room conditions, in particular glass bottles for filling with pharmaceutical products, wherein the containers are, via laminar flow units, continuously moved into and out of a radiant oven and are then cooled by HOSCH-filtered air, a part of the HOSCH-filtered air being branched off at the outlet of the radiant oven and being passed in a controlled low-turbulence displacement flow through the radiant oven.

A method of this type with the associated radiant oven has been described in German Patent 2,631,352, the U.S. counterpart being U.S. Pat. No. 4,140,479 to Edgar Sirch et al, dated Feb. 20, 1979. The sterilization method described therein has proved itself by and large if, with respect to the maximum permissible particle count, the requirements of class 100, US Federal Standard 209 b (or approximately class 3 VDI 2083) are to be fulfilled.

Furthermore, the new edition of this standard, also relevant to pharmaceutical production (US Federal Standard 209 c), also defines the higher-grade class 10 which is to be met by the radiant oven described.

SUMMARY OF THE INVENTION

Starting from this stated aim, the invention is based on the object of still further improving the dry-heat sterilizing method described above, using a radiant oven operating according to the principle of a low-turbulence displacement flow.

Starting from the method described at the outset, this object is achieved according to the invention when the clean-room conditions are maintained in the radiant oven by positive pressure $P_2$ as compared with atmospheric pressure $P_{AT}$ and by a counterflow, resulting therefrom, of a mean flow velocity below 0.2 m/second, positive pressure $P_2$ being measured in the radiant oven and being compared with a set value, and the exit air fan for the HOSCH-filtered cooling air on the exit side being reregulated in such a way that the deviation $\Delta p$ from the set value is minimized, and when the major part of the radiant heater elements—preferably arranged both above and below the bottles—is operated at constant electric power and the temperature fluctuations caused by unsteady operating states are eliminated by controlling the remaining minor part of the heater elements. All pressure data are here to be understood as positive pressure compared with atmospheric pressure $P_{AT}$.

As a result of these combined measures, an undisturbed, low-turbulence displacement flow is maintained in the radiant oven during the entire operating time. It has been found that the pressure in the radiant oven can be utilized as a sensitive and particularly readily processable measured variable for maintaining constant flow conditions at such low flow velocities (<0.2 m/second). The division of the heater power in the radiant heater elements into a proportionately predominant constant load (base load) and a control load which is substantially smaller by comparison ensures that the convection flows interfering with the low-turbulence counterflow are reduced to the technically possible minimum.

Preferably, the set value for the positive pressure $P_2$ in the radiant oven is adjusted to a value of $\geq 0.2$ Pa. With respect to the flow velocity in the radiant oven having a free cross-section of about 0.7 m², a mean Reynolds number below the critical value of 2,300 is thus maintained.

According to a further development of the invention, the clean-room classification in the radiant oven is continuously monitored, and recorded, by means of suction tulips which are in a grid-like arrangement above the glass containers and can be consecutively connected to a particle counter. In this way, the clean-room classification can be reliably monitored during the entire operation.

Advantageously, the sterilization temperature of the glass containers is also directly measured pyrometrically and, if the temperature falls below a predetermined set value, the transport belt is stopped, so that the glass containers can be brought reliably up to the sterilization temperature.

In order to maintain the clean-room conditions also during starting or stopping of the radiant oven, the glass containers are advantageously moved in close packing on the transport belt through the radiant oven and, when the radiant oven is filled or emptied, the diaphragms at the inlet and outlet are readjusted in such a way that the pressure and temperature values, associated with the steady, clean-room conditions, in the radiant oven remain very largely constant.

Convection flows interfering with the displacement flow can also be minimized by rendering the temperature uniform across the full width of the radiant oven by means of additional heater elements integrated into the side walls. Temperature deviations in the material being sterilized are thus also reduced.

Directly at the point where the bottles leave the radiant oven, there is a relatively large pressure step between the pressure level $P_2$ of the radiant oven and the pressure $P_3$ prevailing in the laminar-flow lock formed as a cooling zone. As a result of this pressure step, an injection stream of relatively high flow velocity is generated, which causes interference with the low-turbulence displacement flow in this region. A further improvement can therefore be achieved if the pressure gradient between the cooling zone and the radiant oven is additionally degraded by a laminarization fabric fitted in, whereby the counterflow entering the radiant oven is more quickly rendered quiet and uniform.

The following advantages are obtained by the invention:

1. Systematic particle measurements have shown that extremely low particle counts corresponding to VDI 2083 Class 2 can be maintained in the radiant oven in the critical region above the bottle opening.

2. Based on the instrumented validation and recording, it was also possible to prove that the clean-room conditions indicated above remained constant during the entire operation.

3. In addition, other interfering variables, such as, for example, convection flows caused by temperature inhomogeneities can be reliably intercepted.

4. Control of the flow velocity of the counterflow can be relatively easily realized technically on the basis of a sensitive pressure sensor in the radiant oven and has the advantage of high sensitivity and accurary (small control deviation).

5. Owing to the continuous measurement and recording of all the important operating parameters, the clean-room conditions and sterilization conditions can be continuously ensured and monitored.

6. Furthermore, as compared with the state of the art, the heating power in the radiant oven can be lowered even further by the great reduction in the hot lost mass flow of the air. The method according to the invention thus permits energy savings in radiant ovens in pharmaceutical production plants.

BRIEF DESCRIPTION OF THE DRAWINGS

The invention is illustrated in more detail below by reference to illustrative embodiments and drawings, in which:

FIG. 1 diagrammatically shows the structure of an overall unit for the radiant-heat sterilization of glass containers, FIG. 2 shows a cross-section through the radiant heat tunnel at right angles to the transport direction of the glass containers and FIG. 3 shows the arrangement of the air suction branches above the transport belt for particle measurement.

DETAILED DESCRIPTION OF THE DRAWINGS

In the unit for carrying out the hot-sterilization method according to the invention (according to FIG. 1), four zones are provided, namely the inlet zone I, the drying, heating and sterilizing zone II, the cooling zone III, and the outlet zone IV. The glass containers 1 which are to be sterilized are passed by means of a transport belt through the radiant oven 3 which forms the sterilizing zone II. On its upper and lower sides, the radiant oven 3 is fitted with rod-shaped IR heater elements 4. In addition, further electric heater elements 5 are provided parallel to the side walls (see FIG. 2), which heater elements extend almost over the entire length of the radiant oven and thermally screen the glass containers 1 from the unheated side walls 6 of the radiant oven. This wall protection heating contributes to rendering the temperature uniform in the entire cross-section of the oven and thus prevents interfering lateral convection flows.

The inlet I consists of a laminar-flow lock with a fan 7 which flows against the high-efficiency submicron particulate filter 8 (HOSCH filter) and generates an air curtain at right angles to the transport direction at the inlet of the radiant heat tunnel 3.

At both the inlet and outlet of the radiant oven 3, there are height-adjustable diaphragms 9 and 10 which are set in such a way that just the cross-section of the bottle pack is cleared at the inlet and outlet of the oven. The diaphragm 10 consists of a laminarization fabric, the function of which will be further explained below. At the inlet of the radiant oven 3, that is to say below the inlet diaphragm 9, the air is extracted by means of a fumes/exit air fan 11.

In the cooling zone, a laminar-flow curtain, which serves for cooling the hot glass containers 1 coming out of the radiant oven, is likewise produced by means of the fans 12 and the HOSCH filters 13. The air is here discharged below the transport belt 2 by means of the exit air fan 14. The cooling zone III is adjoined by the outlet zone IV which in turn is fitted with a fan 15 and two HOSCH filters 16. A further height-adjustable diaphragm 17 is arranged between the cooling zone III and the outlet IV.

The sterilizing temperature of the glass containers 1 in the radiant oven can continuously be measured and monitored by a radiation pyrometer 18 which is built into one of the side walls 6 (see FIG. 2). By processing this measured value, it is possible, for example, when the temperature falls below the set value, to stop the transport belt 2 before it runs into the sterilizing section and to bring the containers 1 up to the sterilizing temperature.

In addition, provision is made for directly measuring and recording the particle count in the radiant oven. For this purpose, a multiplicity of air suction branches (so-called suction tulips) 19, which are connected consecutively to a particle counter, are arranged in the radiant oven 3 in a grid-like distribution above the glass containers 1, as shown in FIG. 1, FIG. 2 and FIG. 3. This ensures continuous monitoring and recording of the clean-room conditions in the radiant oven.

In addition, further suction tulips 20 can be provided in the inlet, cooling and outlet zones (see FIG. 1 and FIG. 3).

In view of the required extremely low particle counts in the radiant oven (clean-room class 2 according to VDI guideline 2083, sheet 1, page 4, table 1), the pressure conditions in the radiant oven 3 and the resulting flow fields as well as the temperatures in the radiant oven are of essential importance. In the inlet zone I, there is a slight positive pressure $P_{LF1}$ over atmospheric pressure. Below the inlet diaphragm 9, where the air is extracted by the extraction fan 11, a reduced pressure is generated, which is marked $P_1$. In the radiant oven 3, there is a pressure drop with a very shallow pressure gradient, the pressure in the radiant oven increasing from the left to the right, that is to say with the direction of transport. The pressure prevailing below the outlet diaphragm 10 is marked $P_3$. The pressure $P_3$ should be above the pressure $P_2$ in the radiant oven and the pressure $P_1$ in the inlet. In the cooling zone III, a pressure $P_{KZ}$ prevails which is markedly above the pressure $P_3$ at the outlet diaphragm 10. The highest pressure $P_{LF2}$ is maintained in the outlet zone.

Under these pressure conditions, a small part of the air from the cooling zone III is branched off and flows through the outlet diaphragm 10 against the direction of movement of the containers right through the radiant oven to the extraction point extracted by the fumes/exit air fan 11. The pressure gradient between the radiant oven and the cooling zone is adjusted such that the said counterflow has a flow velocity of <0.2 m/second. Experience shows that, at these low flow velocities, it is difficult to maintain constant flow conditions in the radiant oven.

However, steady stable flow conditions can be achieved even at still lower flow velocities if the positive pressure $P_2$ (as compared with atmospheric pressure) in the radiant oven 3 is controlled. For this purpose, the radiant oven 3 is fitted, approximately in its middle, with a pressure sensor 21 which, as a measuring detector, is a constituent of a control loop. The control is effected in such a way that the pressure sensor 21 detects the deviation $\Delta p$ from a preadjusted set value $P_2$ and, as a function of this deviation, reregulates the speed of rotation of the drive motor 22 for the exit air fan 14 in such a way that the deviation $\Delta p$ from the set value is minimized. By means of the control loop (sensor 21, fan drive motor 22, exit fan 14), the pressure $P_2$ in the radiant oven and hence also the flow conditions can be kept very accurately constant. Whereas a direct measurement of the flow velocity at such low velocities is virtually no longer possible, the pressure control in the radiant oven as described makes it possible reliably to maintain a low-turbulence displacement flow at a velocity of only 5 cm/second to 10 cm/second.

To render the flow uniform at the outlet of the radiant oven 3, the outlet diaphragm 10 consists of a laminarization fabric which provides a pressure-degrading surface of large area. This already ensures the formation of the required low-turbulence counterflow at the outlet from the radiant oven. The laminarization fabric can, for example, be commercially available sintered metal fabric.

In practice, temperature fluctuations caused by unsteady operating states in the radiant oven, cannot normally be avoided without special precautions. Such temperature fluctuations can lead to convection flows in the radiant oven, which are superposed on the low-displacement counterflow and significantly interfere with the latter. The interfering effect is the greater, the lower the velocity of the displacement in the radiant oven. For these reasons, an additional control is provided for the heater power of the radiant oven, the major part of the heater elements 4 being operated at constant electric power (base load) and the temperature fluctuations caused by unsteady operating states are eliminated by controlling the remaining, minor, part of the heater elements (control load). The control load is here in the range from 10% to 20% of the total load.

When starting and stopping the unit, and in the event of other unsteady operating states, disturbances with respect to the flow conditions naturally occur. These disturbances can be minimized if, on the one hand, it is ensured that the glass containers 1 are moved in close packing on the transport belt 2 into the radiant oven 3 and, on the other hand, when the radiant oven is filled and emptied, the diaphragms 9 and 10 at the inlet and outlet, respectively, are readjusted in such a way that the free inflow cross-section is brought to the same value as that when the bottles enter and leave. This makes it easier to keep the pressure in the radiant oven constant and hence to maintain the low-turbulence counterflow.

EXAMPLE

Standard operating conditions for steady operation of the radiant oven under clean-room conditions $P_{LF1}$ Pressure in the LF curtain at inlet I $P_1$ Pressure below the inlet diaphragm 9

$P_2$ Pressure in the radiant oven 3

$P_3$ Pressure below the outlet diaphragm 10

$P_{K2}$ Pressure in the cooling zone III above the transport belt 2

$P_{LF2}$ Pressure in the LF curtain at the outlet II.

All the pressure data are to be understood as positive pressures relative to atmospheric pressure $P_{AT}$.

$P_2 \geqq 0.2$ Pa $P_{LF1} < 2.0$ Pa $P_1 \leqq P_2$ $P_3 > P_2$ $P_3 \leqq P_{KZ}$ $P_{KZ}$ 4 Pa $P_{LF2}$ 10 Pa Dimensions of the radiant oven (FIG. 2 and 3)

length = about 3.0 m width = about 1.5 m height = about 0.5 m

The transport speed of the belt 2 was 16 cm/minute. Under these pressure and temperature conditions and with these dimensions of the radiant oven, an air stream of 170 m$^3$/hour was extracted by the fumes/exit air fan 11. It was thus possible to maintain a displacement flow of a constant velocity of about 7 cm/second in the radiant oven. The sterilizing temperature in the radiant oven was 280° C.

What is claimed is:

1. Method for sterilizing heat-tolerating containers under clean-room conditions, in particular, glass bottles for filling with parenteral medicaments, wherein the containers are, via laminar-flow units, continuously moved into and out of a continuous sterilizer having four successive zones, an inlet zone I, a heating and sterilization zone II, a cooling zone III and an outlet zone IV, each zone having an inlet and an exit end, said sterilizer comprising a radiant oven surrounding zone II to heat the containers which are then cooled in the cooling zone III by HOSCH-filtered air introduced into the cooling zone III under pressure, said radiant oven including two groups of electric powered radiant heat elements, a first of said groups providing a major portion of the desired radiant heat and a second of said groups providing a minor portion of the desired radiant heat, a first and major portion of the HOSCH-filtered air introduced to zone III being removed by a zone III exit fan, and a second and minor portion of the HOSCH-filtered cooling air to zone III being branched off and passed back out from the inlet end of zone III through the radiant oven of zone II in a low-turbulence counterflow from the zone II outlet to the zone II inlet, and said second portion of the cooling air being extracted at the inlet end of the radiant oven zone II by means of a fumes/exit air fan, and wherein said desired clean-room conditions are maintained in zone II by the steps of: maintaining a positive pressure $P_2$, as compared with atmospheric pressure $P_{AT}$, in zone II; maintaining said counterflow through zone II having a mean flow velocity below 0.2 m/second; measuring said positive pressure $P_2$ in zone II; comparing said measured pressure $P_2$ with a predetermined desired pressure value to be maintained; in response to said comparison, regulating the speed of rotation of the zone III exit air fan for the HOSCH-filtered cooling air so that the deviation $\Delta p$ of said actual pressure $P_2$ from said predetermined desired pressure value is minimized; and the additional steps of operating said first portion of the radiant heater elements at constant electric power, and variably controlling electric power to the second portion of the radiant heater elements to eliminate temperature fluctuations and resultant convection flows caused by unsteady operating states of the sterilizer, in order to maintain an undisturbed, low-turbulence counterflow in the radiant oven.

2. Method according to claim 1, comprising the further step of adjusting said predetermined value for the positive pressure $P_2$ in the radiant oven, zone II, to a value of $\geq 0.2$ Pa.

3. Method according to claim 1, further comprising causing the flow velocity provided by the fumes/exit air fan at the inlet end of the radiant oven zone II to be a value with respect to the flow velocity in the radiant oven, that a mean Reynolds number below a critical value of 2,300 is maintained.

4. Method according to claim 1, including the further steps of: continuously monitoring the clean-room conditions in the radiant oven zone II; and recording by means of particle counts using suction tulips in a grid-like arrangement above the glass containers as they are moved through zone II.

5. Method according to claim 1, including the further step of directly measuring, pyrometrically, the temperature of the glass containers while in said zone II; and, if the temperature falls below a predetermined sterilization value, stopping the laminar-flow units until the glass containers have been heated up to said predetermined sterilization temperature.

6. Method according to claim 1, wherein said laminar-flow units include a transport belt through the radiant oven and including the further steps of closely packing the glass containers on the transport belt; moving said closely packed containers through the radiant oven; providing diaphragms at the inlet end and outlet end of zone II; and, when said radiant oven is filled or emptied of said closely packed containers, adjusting said inlet and outlet diaphragms so that the pressure, flow velocity and temperature values required for steady clean-room conditions in the radiant oven zone II remain largely constant.

7. Method according to claim 1, wherein said radiant oven includes side walls, and the method includes the additional step of arranging additional heater elements in front of the interior side surfaces of the side walls of the radiant oven to render uniform a distribution of temperature within the radiant oven.

8. Method according to claim 1, wherein the pressure difference between the pressure in the cooling zone and the pressure in the radiant oven is caused to decrease by using a laminarization fabric at the exit end of zone II, whereby the counterflow passing through the radiant oven from zone III to zone II is rendered quiet and uniform as quickly as possible at the exit end of zone II.

* * * * *

UNITED STATES PATENT AND TRADEMARK OFFICE
CERTIFICATE OF CORRECTION

PATENT NO.   : 5,064,614
DATED        : November 12, 1991
INVENTOR(S)  : ROLAND REISS et al.

It is certified that error appears in the above-identified patent and that said Letters Patent is hereby corrected as shown below:

On the cover page:

In item [73], the second word in the Assignee's name should be --GILOWY--, not "GILOVYY".

Signed and Sealed this

Ninth Day of March, 1993

*Attest:*

STEPHEN G. KUNIN

*Attesting Officer*       Acting Commissioner of Patents and Trademarks